(12) United States Patent
Haveri

(10) Patent No.: US 8,353,295 B2
(45) Date of Patent: Jan. 15, 2013

(54) BRANCHING UNIT AND ARRANGEMENT FOR DELIVERING A RESPIRATORY GAS OF A SUBJECT

(75) Inventor: Heikki Haveri, Huhmari (FI)

(73) Assignee: General Electric Company, Schenectady, NY (US)

( * ) Notice: Subject to any disclaimer, the term of this patent is extended or adjusted under 35 U.S.C. 154(b) by 759 days.

(21) Appl. No.: 12/490,427

(22) Filed: Jun. 24, 2009

(65) Prior Publication Data

US 2009/0320841 A1 Dec. 31, 2009

(30) Foreign Application Priority Data

Jun. 26, 2008 (EP) .................................. 08396010

(51) Int. Cl.
*A61B 5/08* (2006.01)

(52) U.S. Cl. .............................. 128/207.14; 128/207.18

(58) Field of Classification Search . 128/207.14–207.18
See application file for complete search history.

(56) References Cited

U.S. PATENT DOCUMENTS

| | | | |
|---|---|---|---|
| 5,375,592 A * | 12/1994 | Kirk et al. ................ | 128/207.14 |
| 6,298,848 B1 * | 10/2001 | Skog ........................ | 128/204.18 |
| 6,308,706 B1 | 10/2001 | Lammers et al. | |
| 2005/0211253 A1 | 9/2005 | Smaldone et al. | |
| 2006/0201517 A1 * | 9/2006 | Rich et al. ................ | 128/207.14 |
| 2007/0062534 A1 * | 3/2007 | Fisher et al. ............. | 128/205.14 |
| 2007/0062535 A1 * | 3/2007 | Psaros ...................... | 128/205.28 |
| 2008/0251082 A1 * | 10/2008 | Sinha ........................ | 128/207.16 |

FOREIGN PATENT DOCUMENTS

EP 1820528 A1 8/2007

* cited by examiner

Primary Examiner — Stephen Crow
(74) Attorney, Agent, or Firm — Global Patent Operation

(57) ABSTRACT

A branching unit for delivering a respiratory gas of a subject is disclosed herein. The branching unit includes a first limb for delivering an expiratory gas during an expiratory phase and a second limb for delivering an inspiratory gas during an inspiratory phase. The branching unit also includes a third limb for delivering both the expiratory gas and the inspiratory gas and a common branching point for the first limb, the second limb and the third limb. The first limb, the second limb and the third limb include a volume for the respiratory gas and which volume includes both an active volume with the gas exchanging between the inspiratory phase and the expiratory phase and a dead volume for the respiratory gas with insufficient gas exchange from the inspiratory phase to the expiratory phase and the dead volume being less than 1 ml.

13 Claims, 3 Drawing Sheets

Prior art

BRANCHING UNIT AND ARRANGEMENT FOR DELIVERING A RESPIRATORY GAS OF A SUBJECT

CROSS-REFERENCE TO RELATED APPLICATIONS

This application claims priority under 35 U.S.C. §119(a)-(d) or (f) to prior-filed, co-pending European patent application serial number 08396010.4, filed on Jun. 26, 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

This disclosure relates to a branching unit and arrangement for delivering a respiratory gas of a subject.

2. Description of Related Art

Total Lung capacity (TLC) is dependent upon many factors such as a weight, a sex, an age and an activity. For example, females tend to have a 20-25% lower capacity than males. Tall people tend to have a larger total lung capacity than shorter people. Heavy smokers have a drastically lower TLC than nonsmokers. Some people, such as elite athletes, have a TLC well above average.

Tidal volume (TV) is an amount of an air inspired or taken into the lungs in a single breath. TV is also dependent on the sex, size, height, age and a health etc. of a patient. In general TV also decreases as the size of the patient decreases. In an average healthy adult, TV is about 400-600 ml whereas in an average healthy neonate, that measures 3.5-4 kg and is 50 cm tall, TV is approximately 25-50 ml. On the other hand, in an average premature neonate that measures only 500 grams TV is only about 2-3.5 ml. TV of a smaller patient's is very difficult to measure, but it can be approximated to 4-7 ml/kg, applying a general rule of thumb for approximating the TV of the human lung. In practice the TV of the patient suffering pulmonary system deficiency is normally much less than the approximation gives.

When the patient is mechanically ventilated with a conventional ventilator, an endotracheal tube is placed into a trachea so that it goes through oral or nasal cavity and larynx. The other end of the endotracheal tube is connected to a breathing circuit Y-piece through a luer type connector. If the patient is gas monitored with a mainstream or sidestream gas analyzer, an airway adapter used for sampling the breathing gas that is analyzed by the gas analyzer is normally connected between connectors of the endotracheal tube and the breathing circuit Y-piece. During an inspiration the fresh breathing gas including higher oxygen ($O_2$) concentration flows into the patients lungs through an inspiratory limb of the breathing circuit Y-piece, the airway adapter, the endotracheal tube and their connectors, then to a trachea, a bronchus, a bronchi, bronchioles and finally reaching an alveoli deep in the lungs, where all the gas exchange actually occurs. Carbon dioxide ($CO_2$) molecules in a hemoglobin of a blood flowing in tiny blood vessels around the alveoli are replaced with $O_2$ molecules in the fresh breathing gas through the thin walls of the alveoli. $O_2$ molecules take their place in the hemoglobin, whereas $CO_2$ molecules flow out from the patient within the used expired breathing gas, through the same path as the fresh gas came in during the inspiration. Thus a gas concentration of the breathing gas measured by the gas analyzer is somewhat proportional to the gas concentration in the blood.

A volume in a space between a connection of the inspiratory and expiratory limbs of the Y-piece and the patient's mouth or nose, a beginning of oral and nasal cavities, is called a mechanical dead volume or dead space, whereas the volume in a space between patient s mouth or nose and the entrance of alveoli is called an anatomical dead volume. The part of the lung that is injured or damaged for some reason and does not participate for the gas exchange is called more specific a physical dead volume. It is obvious that as the used breathing gas flows out from the patient's lungs through the expiratory limb during expiration, a part of the used gas newer exits a pulmonary system, as well as the patient side of the breathing circuit, but remains in the mechanical and anatomical dead volume. Then as the fresh gas is inspired in to the lungs through the inspiratory limb the used gas already in the anatomical and mechanical dead volume flows into the lungs before the fresh gas. The used gas fills up some or all of the alveoli depending on a ratio of the dead volume and TV or at least mixes up with the fresh gas decreasing the concentration of $O_2$ as well as increasing the concentration of $CO_2$ in the lungs, which in turn decreases the gas exchange in the alveoli. This means that the larger the dead space, the larger the volume of the used gas, with a low $O_2$ and high $CO_2$ concentration, that flows back to the patients lungs during the inspiration and worse the gas exchange in the alveoli. In other words, if the total dead volume were larger than TV or as large as TV, the patient would not get any fresh gas into the lungs, but respires the used gas back and forth in the dead volume. In practice a diffusion of gases assists the gas exchange over the dead volume little, especially when there is some movement of gases such as a high frequency ventilation evolved, but the overall gas exchange in the alveoli would be lethal or dangerously poor anyway.

The anatomical dead volume is almost impossible to reduce, but it is proportional to the size and the physical condition of the patient. The mechanical dead volume depends on a breathing circuit design, an inner diameter of a tubing, connectors and additional accessories, such as sidestream and mainstream gas analyzers Obviously the mechanical dead volume is more critical for smaller patients with smaller TV or patients suffering barotraumas etc., which also decrease TV. In practice the sidestream gas analyzing is not suitable for the patients with very small TV, since in addition to a dead volume increment caused by the airway adapter, conventional sidestream gas analyzers "steal" sample gas from the inspratory and expiratory gas flow, thus decreasing the gas exchange in the alveoli. Furthermore respiration rates (RR) of smaller patients are higher, up to 150 breaths/minute or even more, which is well above the measurement range of the conventional sidestream gas measurement technology, compared to adult patients with RR less than 60 breaths/minute.

Although the conventional mainstream gas analyzers are able to measure higher RR more than 60 breaths/minute with high TV, the analyzer dead volume is even more than that of sidestream gas analyzers. Together with the Y-piece dead space, where the mainstream analyzer is connected to, is much too high to be used with smaller patients. Thus at the moment there does not exist a proper breathing gas concentration analyzing technique for smaller patients. The high overall dead volume together and non existing breathing gas analyzing are also reasons why a conventional ventilation cannot be used in many cases or at least it is difficult or even dangerous to use. Due to the weaknesses of conventional ventilation patients are more likely ventilated with high frequency ventilators (HFV) with RR up to 3000. These ventilators do not have the conventional inspiration and expiration phase as normal respiration, but the gas exchange in the alveoli is ensured through the diffusion of gases. HFV has it own drawbacks in addition that the gas diffusion type high frequency ventilation also makes it impossible to measure breathing gas concentrations comparable to the gas concentration in the alveoli with any conventional gas analyzer technology.

FIG. 1 shows an exploded schematic view of the patient side part of the conventional breathing circuit consisting of the endotracheal tube 1, the Y-piece 2 and a combination of the conventional mainstream type airway adapter 32 and the gas analyzer 3 known in prior art.—The Y-piece comprises three limbs. The inner diameter of the limb that connects to endotracheal tube is approximately 15 mm, whereby a cross-sectional inner area is approximately 180 $mm^2$. The inner diameter of those limbs that connect to ventilator is approximately 19 mm, whereby a cross-sectional inner area is approximately 280 $mm^2$. The airway adapter 32 comprises a sampling chamber 33 in the middle of a female luer connector 34 and a male luer connector 35. The connectors 34 and 35 are conventional standard size connectors, which connection diameter is 15 mm or a cross-sectional area of approximately 180 $mm^2$. The inner diameter of the male luer connector is 13-13.5 mm, a cross-sectional area of approximately 135-145 $mm^2$ and the length 17-28 mm. Female luer connectors fit on male luer connectors in every connection of the breathing circuit, thus the inner diameter is conical approximately from 14.5 to 15.5 mm. The airway adapter 32 is placed into a cavity 36 in the conventional analyzer body 31 so that breathing gases flowing through the breathing circuit and through the sampling chamber 33 in airway adapter 32 can be analyzed by the analyzer body 31. The gas analyzer 3 is connected between the endotracheal tube 1 and the Y-piece 2 through its airway adapter 32. The airway adapter 32 connects through the male connector 35 to a female connector 21 of the Y-piece 2 and similarly the female connector 34 of the airway adapter 32 connects to a male connection of separate connector 11, which further connects to the endotracheal tube 1 through a tubular connection.

The inner diameter of endotracheal tube 1 can vary from 2 mm to 10 mm or more or in terms of a cross-sectional area approximately from 3 to 79 $mm^2$ or more and the length can vary from 150 mm to 250 mm or more depending on the patient it is connected to. In general the inner diameter (ID) of the endotracheal tube 1 increases as the age (or the size proportional to the age) of the patient increases. In general the smaller the patient the smaller the endotracheal tube 1 used. Table 1 below shows some recommendations for the use of endotracheal tubes with different aged patients from manufacturers.

TABLE 1

| Uncuffed tube ID [mm] | Cuffed tube ID [mm] | Age [years] | | |
|---|---|---|---|---|
| 2.0 | | | | |
| 2.5 | | | | |
| 3.0 | 3.0 | <1 (<3 kg) | | |
| 3.5 | 3.5 | 1-2 | Neonatal | |
| 4.0 | 4.0 | 2-4 | | |
| 4.5 | 4.5 | 4-6 | | |
| 5.0 | 5.0 | 6-8 | | Pediatric |
| 5.5 | 5.5 | 8-10 | | |
| 6.0 | 6.0 | 10-12 | | |
| 6.5 | 6.5 | 12-14 | | |
| 7.0 | 7.0 | 14-16 | | |
| | 7.5 | >16 | | Adult |
| | 8.0 | | | |
| | 8.5 | | | |
| | 9.0 | | | |
| | 9.5 | | | |
| | 10.0 | | | |

Thus the connectors 11 are conventionally used to connect very different size of the endotracheal tubes 1 to one size of the airway adapter 32, which means that each size of endotracheal tube 1 needs a separate connector 11 connected to it. Other end of the connector 11 is a standard size male connector that fits in to the female connector 34 of the airway adapter 32 and the other end is tubular connector that fits to it's respective endotracheal tube. The total length of the connector 11 is approximately 31 mm, the length of the tubular part approximately 9 mm and the length of the male connector approximately 22 mm.

FIG. 2 shows a schematic view of the breathing circuit already shown in FIG. 1 as all the separate parts are connected together. The mechanical dead volume of the conventional breathing circuit is the volume between places 13 and 24, shown with dashed lines in FIG. 2. The place 13 on the endotracheal tube 1 is the place where the endotracheal tube 1 comes out from the nasal or oral cavity of the patient and the place 24 is a cross section where the inspiratory limb 22 and the expiratory limb 23 of the Y-piece 2 connect to the connector 21. The volume of the endotracheal tube 1 consists of the volume of the connector 11 and the volume of the endotracheal tube 1 sticking out from the patient. The dead volume of the connector 11 is approximately 2-3 ml alone. The volume of the airway adapter 32 depends on the length and the inner diameter of the sampling chamber 33 added with the volume what is left of the connector 34 as the connector 11 connects to it and with a volume of connector 35, which all depend on the design of different manufacturers. The inner diameter and the length of the sampling chamber 33 becomes from the technical requirements of the gas measurement. That then determines the length and the outer diameter of airway adapter 32, which in turn determines the size of an analyzer body 31 of the gas analyzer 3, which fits on the airway adapter 32. The cross sectional shape of the channel of conventional airway adapters, in to the direction of the gas flow, is rectangular. Regardless of the size of the patient the airway adapter is connected, the width of the channel is 8-10 mm in to the direction in which the gas is analyzed, whereas in to the other direction it is 10-13 mm. The cross-sectional area of the channel is thus approximately 80-130 $mm^2$. The length of the channel, in to the direction of the gas flow, varies between 22-32 mm. The dead volume of the conventional airway adapters is usually much more than 1 ml, around 4-5 ml. The dead volume of the conventional Y-piece 2 becomes mainly from the volume of the connector 21, which is approximately 2-3 ml. Theoretically, a small dead volume around the cross section of the inspiratory limb 22 and the expiratory limb 23 where the inspiratory and expiratory gases mix can be added to the total dead volume of the Y-piece 2.

Conventional mainstream gas analyzers, as well as airway adapters connected to them, are big and heavy, which is one of the disadvantages when used with the smaller patient. Another disadvantage are badly designed connections between different parts of the breathing circuit, such as a step like changes in the flow path that cause turbulences in to the breathing gas as well as gas pockets between connectors that cause further mixing, but also rapid decrease in the flow velocity of the gas which increases the response time. As an example the cross-sectional area of the endotracheal tube, which inner diameter is 2 mm, is approximately 3 $mm^2$, whereas the cross-sectional area of the male connector at the end of the endotracheal tube is approximately 110 $mm^2$. Furthermore the cross-sectional area of the female connector of the airway adapter, where the endotracheal tube is connected to is approximately 180 $mm^2$. As can be seen the ratio between cross sectional areas within the breathing gas flow path is enormous. Every step like change causes turbulences, which mix up inspiratory and expiratory edges and gas pockets cause additional gas concentration offset as the old gas with different gas concentration accumulated into the gas pockets mixes up with the new gas. Furthermore as the inspiratory gas comes out from the patient through the tiny endotracheal tubing in to the large volume of the male connector and female connector of the airway adapter the flow velocity of the gas decelerates rapidly just before the sampling chamber, where the gas concentration measurement occurs. In addition to the turbulence the step like changes cause the deceleration of the gas flow degrades the response time to gas concentration changes even more, which can be seen especially as the RR increases. The biggest step like change is the difference in the inner diameter between the endotracheal tube used with smaller patients (2-4.5 mm, cross-sectional area of 3-16 $mm^2$) and the female connector of airway adapter (15 mm with cross-sectional area of 180 $mm^2$). Rest of the connections generates smaller steps into the breathing gas flow path, but the airway adapter also includes gas pockets. Although the problem is biggest with smaller diameter endotracheal tubes, the same problem occurs also with larger endotracheal tubes. For example the cross sectional area of the endotracheal tube, which inner diameter is 7 mm, is approximately 38 $mm^2$. This is still about ¼ compared to the cross sectional area of 180 $mm^2$ of the female connector at the airway adapter, where the endotracheal tube is connected to.

However, one of the biggest disadvantages for the patient is the large dead volume of Y-pieces and conventional airway adapters and the whole patient side part of the conventional breathing circuit where the gas analyzer is connected. The total dead volume of such conventional breathing circuit, the Y-piece, the airway adapter and endotracheal tube with connector, as was described earlier and shown in FIGS. 1 and 2, which is further connected to the patient that weights 1 kg through the endotracheal tube with the inner diameter of 2.5 mm is at best more than 7 ml. This is approximately one to two times higher than TV of the patient in this example, which is approximately 4-7 ml. This means that the patient in the above example rebreaths the used gas and is more likely to suffer from the poor gas exchange than to get better treatment Thus at the moment there does exist no suitable patient side part of the breathing circuit as well as Y-piece and airway adapter for the breathing gas concentration measurement, at least for small neonatal and premature neonatal patients who have small TV, but the existing configuration could be better for larger patients as well.

The large dead volume of the conventional breathing circuits, the Y-pieces and the airway adapters is one of the biggest and common disadvantages in respiratory care, since the large dead volume interferes the gas exchange in the lungs as the breathing circuit rather than the lung is ventilated and the patient is rebreathing the used gas. Thus small, intubated patients are often ventilated with high frequency ventilators (HFV) with very high respiration rates up to 3000 breaths/min. The high frequency ventilation does not comprise the normal inspiration and expiration phase, but is more like a vibration and the diffusion of the gases, which makes it impossible to gas monitor the patient with the conventional gas analyzing techniques. Moreover the high frequency ventilators are noise and their functionality disputed. The only way to analyze the gas exchange in the lungs is to measure $CO_2$ and $O_2$ concentration from the blood through blood samples or a transcutaneous measurement. The blood sampling is very stressful and even dangerous for the small patient whose blood volume is very small. The trancutaneous measurement has its own weaknesses, such as a need for connections to the patient's skin so that oxygen in the blood just under the skin can be measured. Especially the skin of premature neonates is very thin and fragile and thus the measurement is not very often used. Connections also come loose from the patient easily and the technique is such that it heats up the patient at the connections, which place thus has to be changed. The blood sampling is not a real time measurement, as it has to be analyzed in the laboratory, which in turn causes a long time delay into an acute patient care. As there is no real time measurement to analyze the gas exchange of small patients, they are usually ventilated insufficiently, which causes different trauma for the patient and a longer time to recover.

BRIEF SUMMARY OF THE INVENTION

The above-mentioned shortcomings, disadvantages and problems are addressed herein which will be understood by reading and understanding the following specification.

In an embodiment a branching unit for delivering a respiratory gas of a subject includes a first limb for delivering an expiratory gas during an expiratory phase, a second limb for delivering an inspiratory gas during an inspiratory phase and a third limb for delivering both the expiratory gas and the inspiratory gas. The branching unit for delivering a respiratory gas of a subject also includes a common branching point for the first limb, the second limb and the third limb. The first limb, the second limb and the third limb include a volume for the respiratory gas and which volume includes both an active volume with the gas exchanging between the inspiratory phase and the expiratory phase and a dead volume for the respiratory gas with insufficient gas exchange from the inspiratory phase to the expiratory phase and the dead volume being less than 1 ml.

In another embodiment, a branching unit for delivering a respiratory gas of a subject includes a first limb for delivering an expiratory gas towards a ventilator during an expiratory phase, a second limb for delivering an inspiratory gas coming from the ventilator during an inspiratory phase and a third limb for delivering both the expiratory gas coming from the subject towards the first limb and the inspiratory gas coming from the second limb towards the subject. The branching unit for delivering a respiratory gas also includes a common branching point for the first limb, the second limb and the third limb. The first limb and the second limb is configured to include an active volume for the respiratory gas with the gas exchanging between the inspiratory phase and the expiratory phase, and the third limb is adapted to include a dead volume for the respiratory gas with insufficient gas exchange from the inspiratory phase to the expiratory phase and the dead volume being less than 1 ml.

In yet another embodiment an arrangement for delivering a respiratory gas of a subject includes a branching unit having a first limb for delivering an expiratory gas during an expiration phase, a second limb for delivering an inspiratory gas during an inspiratory phase, a third limb for delivering both the expiratory gas and the inspiratory gas and a common branching point for the first limb, the second limb and the third limb. The arrangement for delivering a respiratory gas of a subject also includes an airway adapter having a sampling chamber and an optical window and which airway adapter can be used while measuring at least one gas component of the respiratory gas and which airway adapter is in flow communication with the branching unit. The branching unit and the airway adapter together include a volume for the respiratory gas and which volume includes both an active volume with the gas exchanging between the inspiratory phase and the expiratory phase and a dead volume for the respiratory gas with insufficient gas exchange from the inspiratory phase to the expiratory phase and the dead volume being less than 5 ml.

Various other features, objects, and advantages of the invention will be made apparent to those skilled in art from the accompanying drawings and detailed description thereof.

DETAILED DESCRIPTION OF THE INVENTION

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

Figure 1:
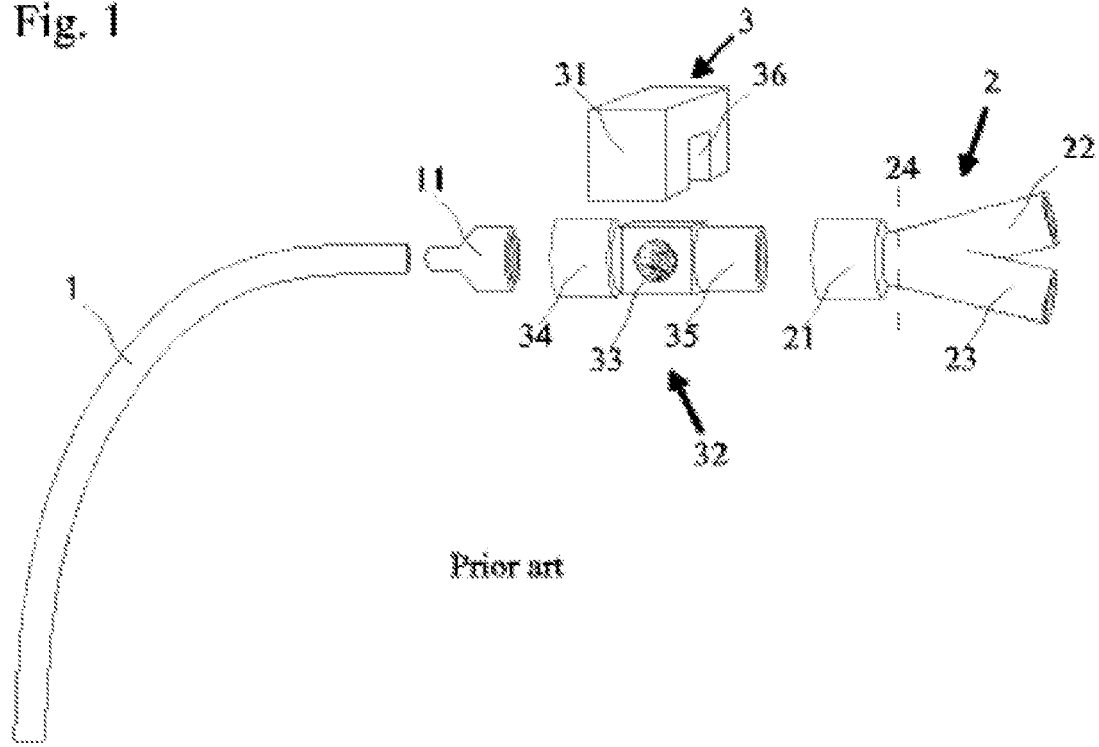
FIG. 1 shows an exploded view of a prior art breathing circuit.
Figure 2:
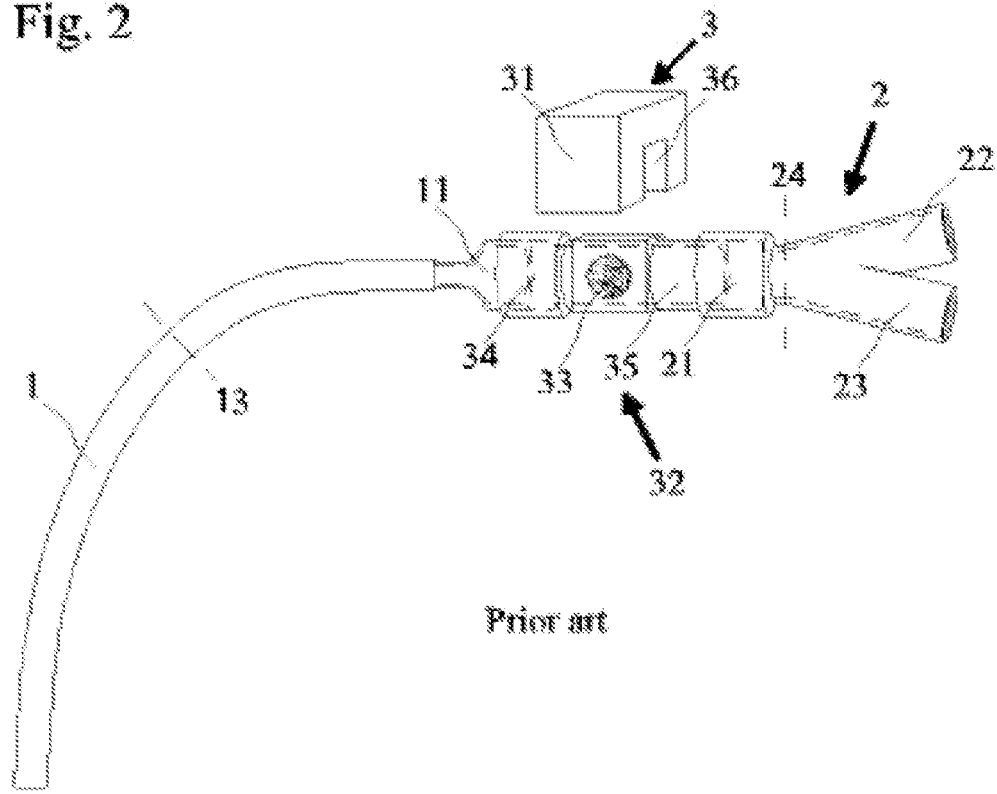
FIG. 2 shows the prior art breathing circuit of FIG. 1 and its dead volume when separate parts are connected together.
Figure 3:
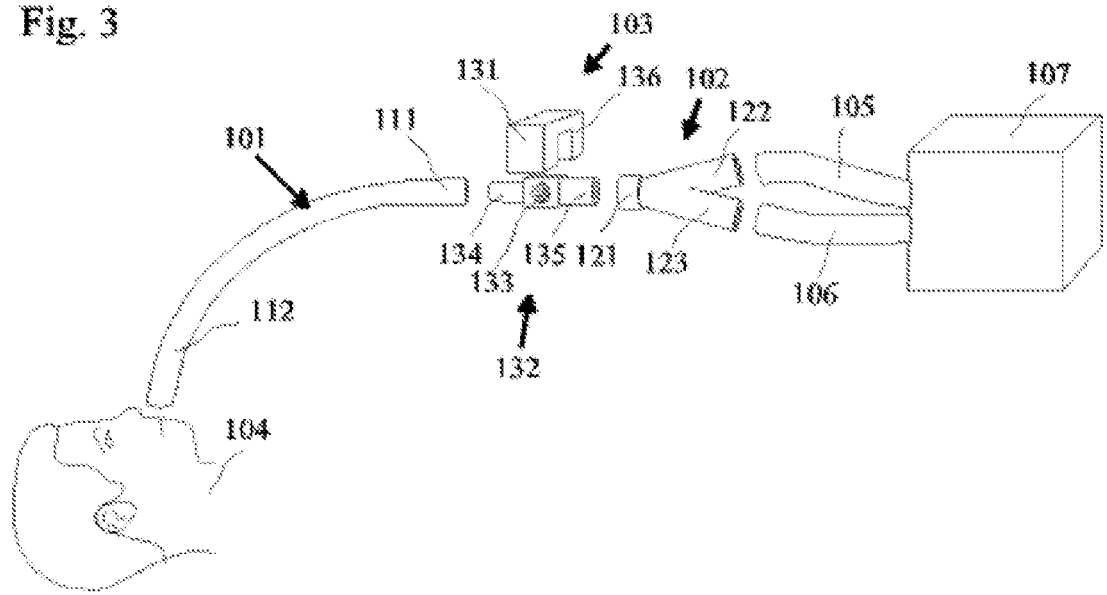
FIG. 3 shows an exploded schematic view of a breathing circuit in accordance with an embodiment.

FIG. 3 shows an exploded schematic view of a breathing circuit including a branching unit 102 such as a Y-piece and an airway adapter 132 connectable to a gas analyzer 103 such as a mainstream gas analyzer according to an embodiment. The airway adapter 132 and the branching unit 102 are in a flow communication with an endotracheal tube 101 insertable into lungs of a subject 104. The breathing circuit and especially the branching unit 102, the airway adapter 132 and the endotracheal tube 101 include a volume for a respiratory gas including both an active volume and a dead volume. The active volume includes such respiratory gas, which is exchanged between an inspiratory phase and an expiratory phase. This means that the subject is inhaling the gas including fresh oxygen with low carbon dioxide concentration close to 0 volume-%. The dead volume includes the respiratory gas, which is insufficiently exchanged between the inspiratory phase and the expiratory phase. Thus the dead volume includes more than normal carbon dioxide concentration, but lower oxygen concentration for the inspiration phase. The gas concentration of carbon dioxide in the dead volume increases, whereas the gas concentration of oxygen decreases relatively to the decrease of TV of the patient. When the tidal volume (TV) and the dead volume of the breathing circuit equal and if the diffusion of gases or further mixing is disregarded the patient is rebreathing the same air back and forth. The concentration of carbon dioxide, as well as the concentration of oxygen, in the dead volume saturates to the concentration of carbon dioxide and oxygen in the patient's alveoli in the lung. Obviously the gas exchange remains poor if the TV is smaller than the dead volume of the breathing circuit. When the TV increases compared to the dead volume of the breathing circuit the gas exchange improves linearly at least according to simplification made above or inversely the gas exchange improves linearly as the dead volume of the breathing circuit is decreased relative to the TV of the patient.

The lungs are critical to maintain acid-base balance. The lungs are very volatile, and they quickly eliminate carbonic acid in the form of carbon dioxide and water. Respiratory acidosis occurs when the carbon dioxide is retained. The $CO_2$ concentration reaches a maximum at the end of exhalation, which is called end-tidal carbon dioxide concentration or tension depending on whether it is expressed in fractional concentration or mmHg. End-tidal carbon dioxide reflects $CO_2$ concentration of alveoli emptying last. The normal value of $ETCO_2$ is around 5 volume-% or 35-37 mm Hg. The gradient between the blood $CO_2$ ($PaCO_2$) and exhaled $CO_2$ is usually 5-6 mm Hg, thus normal value of $PaCO_2$ is approximately 35-45 mmHg. A rise in the partial pressure of $CO_2$ will cause offloading of oxygen from hemoglobin, which is known as the Bohr Effect. Although the body requires oxygen for metabolism, low oxygen levels do not stimulate breathing, but instead is stimulated by higher carbon dioxide levels. Too high carbon dioxide levels shut down the respiratory center and cause acute carbon dioxide toxicity.

In a normal situation a human breath atmospheric air straight through the oral or nasal cavity into the pulmonary system and there does not exist any further tubing or mechanical systems connected to that, which cause rebreathing and disturb the normal gas exchange deep in the lung. The Earth's atmosphere includes roughly (by molar content/volume) 78.08% nitrogen, 20.95% oxygen, 0.93% argon, 0.038% carbon dioxide. This inhaled gas mixture ensures the optimum gas exchange in the human lungs and the optimum acid-base balance in the body. Due to the health risks associated with carbon dioxide exposure, the U.S. Occupational Safety and Health Administration says that average exposure for health adults during an eight-hour work day should not exceed 5,000 ppm (0.5%). The maximum safe level for infants, children, the elderly and individuals with cardio-pulmonary health issues is significantly less. For a short-term (under ten minutes) exposure, the U.S. National Institute for Occupational Safety and Health (NIOSH) and American Conference of Government Industrial Hygienists (ACGIH) limit is 30,000 ppm (3%). NIOSH also states that carbon dioxide concentrations exceeding 4% are immediately dangerous to a life and a health. According to known facts we can determine that the highest inhaled concentration of $CO_2$ for adults having health problems should be less than 1 volume-%, preferably less than 0.5 volume-%. Since there can not be found any exact data for determining the inhaled $CO_2$ concentration level for children having health problems we can assume that the highest concentration of $CO_2$ for pediatrics and neonates may be less than 0.5 volume-%, but preferable less than 0.2 volume-%. Thus this means that the maximum breathing circuit dead volume for the adults must be lower than 1/10 of the TV, whereas for pediatrics and neonates it should be less than 1/25 of the TV.

The branching unit 102 and the airway adapter 132 are designed specially for small subjects such as pediatric, neonates and premature neonates up to high RR such as 200 breaths/minute or even higher, but they can be used with larger subjects such as adults as well. The size of the gas analyzer 103 and the airway adapter 132 together is approximately 12×15×25 mm, which is only about 1/8 of the size of conventional devices and weight approximately 5-10 g, which is less than 1/6, of the weight of conventional devices.

When the respiratory gases are analyzed the airway adapter 132 is preferably connected between the endotracheal tube 101 and the branching unit 102. The branching unit is connected between the airway adapter 132 and a ventilator 107. The branching unit 102 comprises a first limb 123 for delivering an expiratory gas during the expiration phase, a second limb 122 for delivering an inspiratory gas during the inspiration phase and a third limb 121 for delivering both the expiratory and inspiratory gas. The third limb 121 is connected to either the airway adapter or the endotracheal tube 101. The second limb 122 is equipped with a standard luer type male connector (not shown in the Figures) that fits into a standard inspiratory tubing 105 of the breathing circuit. The first limb 123 is also equipped with a standard luer type male connector (not shown in the Figures) that fits into a standard expiratory tubing 106 of the breathing circuit. Another end of both the inspiratory tubing 105 and the expiratory tubing 106 is connected to the ventilator 107. The branching unit 102 may be any other type as well for example such that it fits into a coaxial breathing circuit tubing (not shown in the Figures). The coaxial breathing circuit tubing comprises an inner tubing, for the inspiratory gas to flow towards the patient, placed middle inside an outer tubing so that the expiratory gas can typically flow in the space between the inner and outer tubing from the subject towards the gas exit.

An inner diameter of the endotracheal tube 101 may vary between 2 mm-4.5 mm for neonates, between 5 mm-7 mm for pediatrics and over 7 mm for adults, as was shown in table 1, thus to do a total dead volume minimization each size of the endotracheal tube 101 should have an individual the branching unit 102 and airway adapter 132 designed for it. According to the embodiment an inner diameter of the third limb 121 of the branching unit 102 or an inner cross-sectional area of the third limb 121 of the branching unit 102 has been made as small as possible to make the dead volume of the branching unit 102 as small as possible without, however, causing too high flow resistance for the subject. The diameter or the cross-sectional area depends of a size of the subject, but also if the branching unit is connected straight to the endotracheal tube of the subject or if it is connected to the endotracheal tube of the subject through the airway adapter of the mainstream gas analyzer.

If the subject is neonate and the branching unit is connected straight to the endotracheal tube of the subject there may be advantageously six different branching units 102 with suitable outer diameters or inner cross-sectional areas of the third limb 121 that fit and connect into different size of endotracheal tubes 101 for neonates. With this arrangement the inner diameter or the cross sectional area of endotracheal tubing and the third limb of the branching unit remain constant throughout the whole flow path. The dead volume of the branching unit remains as small as possible, less than 0.15 ml, throughout all size of the subjects in the neonate group.

If the subject is neonate and the branching unit is connected to the endotracheal tube 101 of the subject via the airway adapter 132 of the mainstream gas analyzer 103 there may be advantageously one branching units 102 with one outer diameter or inner cross-sectional area of the third limb 121 that connect to the airway adapters of the mainstream gas analyzer that in turn connect to the endotracheal tubing of all sizes of the subject in the neonate group. The connection between the airway adapter 132 and the third limb 121 overlaps completely to keep the breathing gas flow path linear and to minimize restrictions. For neonates the inner mean diameter of the breathing gas flow path through the third limb 121 can be 4.5 mm-5 mm or the inner mean cross-sectional area 16 $mm^2$-20 $mm^2$, which corresponds to the largest size endotracheal tubes of neonate group. The dead volume of the branching unit 102 or its third limb 121 can be less than 0.2 ml, which dead volume, however, combines with the dead volume of the airway adapter 132 when the third limb 121 of the branching unit 102 is connected to the airway adapter, because the connection overlaps completely.

It is advantageously the same thing with the pediatrics. So the inner mean diameter or the cross-sectional area of the third limb 121 is increasing when the size of the subject is increasing. When the branching unit is connected straight to the endotracheal tube of the subject there may be advantageously five different branching units 102 with suitable outer diameters or inner cross-sectional areas of the third limb 121 that fit and connect into different size of endotracheal tubes 101 for pediatrics. With this arrangement the inner diameter or the cross sectional area of endotracheal tubing and the third limb of the branching unit remain constant throughout the whole flow path. The dead volume of the branching unit remains as small as possible, less than 0.5 ml, throughout all size of the subjects in the pediatric group.

When the branching unit is connected to the endotracheal tube of the subject through the airway adapter of the mainstream gas analyzer there may be advantageously one branching units 102 with one outer diameter or inner cross-sectional area of the third limb 121 that connect to the airway adapters of the mainstream gas analyzer that in turn connects to the endotracheal tubing of all sizes of the subject in the pediatric group. The connection between the airway adapter 132 and the third limb 121 overlaps completely to keep the breathing gas flow path linear and to minimize restrictions. For pediatrics the inner mean diameter of the breathing gas flow path through the third limb 121 can be—approximately 7 mm or the inner mean cross-sectional area 38 $mm^2$-44 $mm^2$, which corresponds to the largest size endotracheal tubing of pediatric group. The dead volume of the branching unit 102 or its third limb 121 can be less than 0.2 ml, which dead volume, however, combines with the dead volume of the airway adapter 132 when the third limb 121 of the branching unit 102 is connected to the airway adapter, because the connection overlaps completely.

Because of the overlapping connection between the airway adapter 132 and the third limb 121 the thickness of the walls of connector 135 of airway adapter 132, which slides into the third limb 121 when connected, should be added to the inner mean diameter of the third limb 121. Thus the inner mean diameter of the third limb 121 can be between 7 mm and 10 mm or the inner mean cross-sectional area should be between 38 $mm^2$ and 80 $mm^2$ for pediatrics. Similarly for neonates the inner mean diameter of the third limb 121 can be between 4.5 mm and 7, 5 mm or the inner mean cross-sectional area should be between 16 $mm^2$ and 44 $mm^2$.

The TV of the smallest pediatric patient weighting 20 kg and intubated with an endotracheal tube with inner diameter of 5 mm (6 years old from the table 1) can be approximated to 80-140 ml. Derived from that the dead volume for the whole breathing circuit should be less than ⅟₂₅ of the TV, which is approximately 3-5 ml. Thus the dead volume of the branching unit 102 or its third limb 121 should be much less than 5 ml, but preferably less than 3 ml for pediatrics, since the total dead volume is divided between the endotracheal tube, the branching unit and the airway adapter, if it is used. Advantageously the smallest dead volume for the whole breathing system for a neonate weighting about 3.5 kg and intubated with an endotracheal tube with inner diameter of 2.5-3 mm should be less than ⅟₂₅ of the TV, which is approximately 0.5-1 ml, but preferably it should be less than 0.25 ml to be able to use it with patients weighting less than 1 kg also. Thus as the total dead volume is divided between the endotracheal tube, the branching unit and the airway adapter when used, the dead volume of the branching unit for neonates should be much less than 1 ml or even better than 0.5 ml, but preferably less than 0.25 ml.

The gas analyzer 103 comprises an analyzer body 131, which is extremely small and low weight enabling totally new design for the airway adapter 132 as well as for the whole patient side of the breathing circuit. The airway adapter 132 comprises a sampling chamber 133, which is advantageously tubular, a male type conically shaped tubular connector 134 that fits straight into the endotracheal tube 101 with a minimal step in a flow path and a male type conically shaped tubular connector 135 that fits the branching unit 102 also with a minimal step in the flow path to avoid turbulences and gas pockets that slow down a measurement. The airway adapter 132 may be integrated into the branching unit 102 to form one complete part to decrease the dead volume, but separate parts may be more usable.

Differences in the dead volume between airway adapters 132, at least within one of the each three different groups of neonates, pediatrics and adults shown later in table 3 is so small that it may be economically unwise to have so many totally different airway adapter designs (shown later in table 2) and branching unit designs. Thus it may be more economical and technically transparent to divide the airway adapters 132 to three different groups of designs also, one for neonates, one for pediatrics and one for adults.

Common for all of these three different groups of the airway adapter designs is the distance across the gas column inside the airway adapter, into the direction of the gas concentration measurement. Advantageously that has to remain constant throughout all airway adapter designs to enable correct measurement without recalibrating the gas analyzer 103 as the airway adapter 132 is changed. On the contrary the cross sectional area of the tubular sampling chamber 133 inside the airway adapter 132 should increase as the subject's size increases to ensure as low flow resistance as possible in the breathing gas flow path. The cross sectional area of the sampling chamber 133 and the connector 135 into the direction of gas flow may be common for all airway adapters within each group of designs, but the connector 134 fits different sizes of the endotracheal tubes 101.

Figure 4:
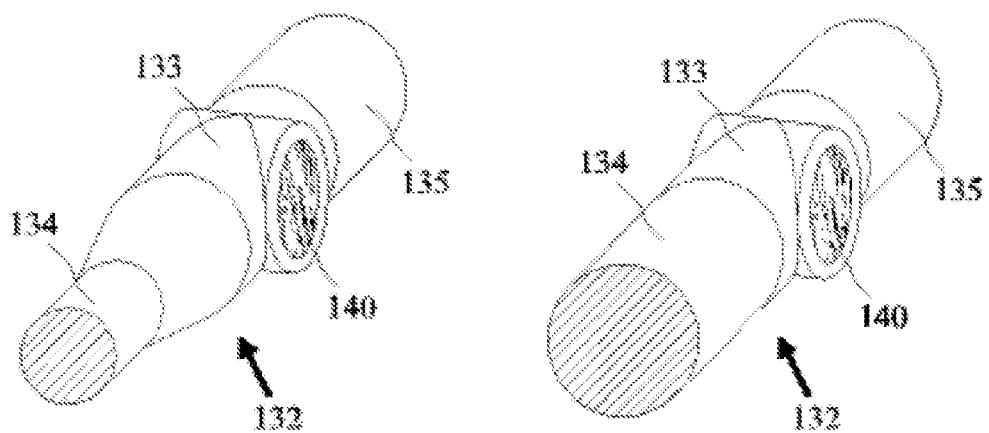
FIG. 4 shows a schematic view of two different airway adapter for neonates.
Figure 5:
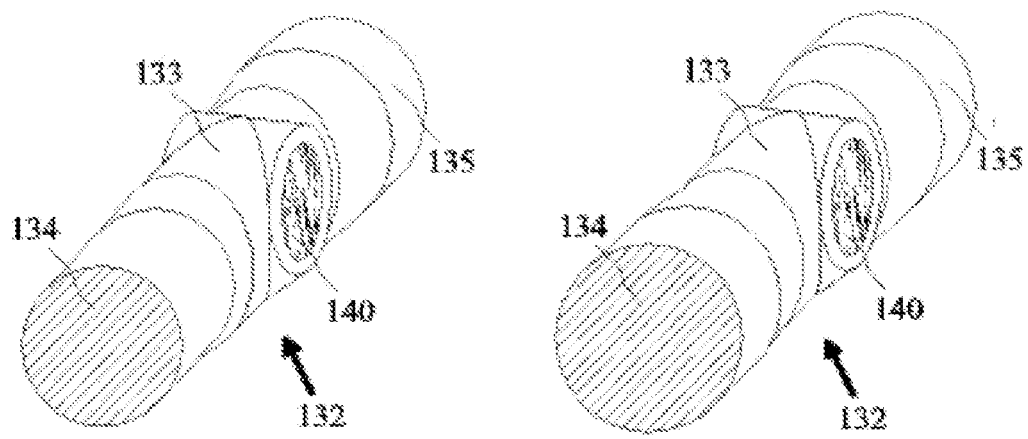
FIG. 5 shows a schematic view of two different an airway adapter for pediatrics.

FIG. 4 shows schematic views of smallest and largest size of the airway adapters 132 for neonates whereas FIG. 5 shows schematic views of smallest and largest size of the airway adapters 132 for pediatrics. Airway adapters 132 of FIG. 4 having minimal dead volume for neonates designed to fit the endotracheal tubes of 2 mm on the left hand of FIG. 4 and 4.5 mm on the right hand of FIG. 4. The tubular sampling chamber 133 inside the airway adapter has a constant inner diameter of approximately 5 mm and a length approximately 12 mm or less. The length may be dependent on the size of the gas analyzer 103. Round optical windows 140 are positioned symmetrically to each other at opposite sides of the airway adapter 132 with a constant distance of approximately 5 mm. The gas measurement occurs through these optical windows 140 and through the gas column between the windows 140. The tubular sampling chamber 133 changes to tubular male connector 135, which inner diameter is approximately 5 mm and length is 8 mm or less that fits into the third limb 121 of the branching unit 102. At the opposite end of the airway adapter 132 the sampling chamber 133 changes to the tubular male connector 134 that fits into the endotracheal tube 101 with 2 mm inner diameter shown on the left hand of FIG. 4.

Similarly on the right hand of FIG. 4 there is shown the tubular male connector 134 that fits into the endotracheal tube 101 with 4.5 mm inner diameter. The length of the male connector 134 is approximately 8 mm or less. The male connectors 134 and 135 fit into the endotracheal tube 101 and the branching unit 102 with a minimal step in the flow path to avoid turbulences and gas pockets that slow down and cause offset into the measurement.

Although FIG. 4 shows the minimum and maximum connectors 134 into 2 mm and 4.5 mm endotracheal tubes respectively the male connector 134 has six different outer diameters at 0.5 mm intervals in diameter (inner diameters as well) to fit the airway adapter 132 into the endotracheal tubes 101 between 2 mm and 4.5 mm also. These six different sizes of the airway adapters 132 for neonates may be produced economically with only one plastic mold comprising a changeable piston to produce six different connectors 134 in connection with a common part for all. Thus the airway adapters 132 may be otherwise symmetrical, but the inner and outer diameter of the male connector 134 changes at 0.5 mm intervals as the piston is changed. Thus six variables of otherwise symmetrical airway adapter can be manufactured with only one tooling.

Schematic views of the minimal dead volume airway adapters 132 for pediatrics designed to fit endotracheal tubes of 5 mm are shown on the left hand of FIG. 5 and 7 mm are shown on the right hand of FIG. 5. The cross sectional area of the tubular sampling chamber 133 perpendicular to the direction of the gas flow is approximately elliptical or rectangular with rounded corners. The inner diameter of the sampling chamber 133 between the round optical windows 140, which are positioned symmetrically to each other at opposite sides of the airway adapter 132 in the direction of the gas measurement is approximately 5 mm. The diameter perpendicular to the direction of the gas measurement is approximately 8 mm.

The minimum cross sectional area of sampling chamber 133 must at least equal to the cross sectional area of endotracheal tube 101 with the inner diameter of 7 mm to ensure enough low flow resistance. The length of the sampling chamber 133 is approximately 12 mm or less. The tubular sampling chamber 133 changes to the tubular male connector 135, which inner diameter is approximately 7 mm and length approximately 8 mm or less that fits into the third limb 121 of the branching unit 102. At the opposite end of the airway adapter sampling chamber 133 changes to the tubular male connector 134 that fits into the endotracheal tube 101 with 5 mm inner diameter on the left hand of FIG. 5.

Similarly on the right hand of FIG. 5 there is shown the tubular male connector 134 that fits into the endotracheal tube 101 with 7 mm inner diameter. The length of the male connector 134 is approximately 8 mm or less. The male connector 134 fit into the endotracheal tube 101 and the male connector 135 into the branching unit 102 with a minimal step in the flow path to avoid turbulences and gas pockets that slow down and cause an offset into the measurement. Although FIG. 5 shows minimum and maximum connectors 134 into the endotracheal tubes 101 respectively the male connector 134 has five different outer diameters at 0.5 mm intervals (inner diameters as well) to fit the airway adapter 132 into the endotracheal tubes 101 between 5 mm and 7 mm also. These five different sizes of the airway adapters 132 for neonates may be produced economically with only one plastic mold comprising a changeable piston to produce five different connectors 134 in connection with a common part for all. Thus the airway adapters 132 may be otherwise symmetrical, but the inner and outer diameter of the male connector 134 changes at 0.5 mm intervals as the piston is changed. Thus five variables of otherwise symmetrical airway adapter 132 can be manufactured with only one tooling.

The sampling chamber 133 inside airway adapters 132 and the connectors 134 and 135, is smooth with minimal step like changes along the breathing gas flow bath to avoid turbulences in the breathing gas flow thus enabling the measurement at high RR such as 200 breaths/minute. The connector 134 fits the endotracheal tube 101, which is the tube made of a material such as polyurethane or similar that does not react chemically with respiratory gases such as anesthetics etc., forming a continuous cavity with a minimal step like change between the inner diameter of the endotracheal tubes 101 and the airway adapters 132 to minimize turbulences and flow velocity decelerations in the breathing gas flow. As an example the cross-sectional area of the endotrachleal tube 101, which inner diameter is 2 mm, is approximately 3 mm$^2$ connects to the airway adapter 132 designed for the neonate group, which largest cross-sectional area inside the airway adapter is only approximately 16 mm$^2$-20 mm$^2$. The ratio in the cross-sectional area is more than ten times better compared to the conventional solutions. When the largest endotracheal tube of the neonate group with the inner diameter of 4.5 mm and the cross-sectional area approximately 16 mm$^2$ connects to the corresponding airway adapter 132 designed for the neonate group the cavity or the flow path is completely uniform. The same applies to endotracheal tubes 101 and airway adapters 132 in the pediatric group. When the smallest endotracheal tube of the pediatric group with the inner diameter of 5 mm and inner cross sectional area approximately 20 mm$^2$ connects to the corresponding airway adapter 132 designed for pediatric group, which largest cross sectional area inside the airway adapter is only approximately 38 mm$^2$-44 mm$^2$, the ratio in cross sectional area is more than five times better compared to the conventional solutions. Similarly when the largest endotracheal tube of the pediatric group with the inner diameter of 7 mm and the cross-sectional area approximately 38 mm$^2$ connects to the corresponding airway adapter 132 designed for the pediatric group the cavity or the flow path is completely uniform. Thus the inner cross-sectional area of the airway adapter 132 should be less than 6 times, but preferably less than 4 times, larger than a inner cross-sectional area of the endotracheal tube 101 used for the same subject group. Furthermore the dead volume of the airway adapter should be much less than 5 ml, but preferably less than 3 ml for pediatrics, since the total dead volume is divided between the endotracheal tube, the branching unit and the airway adapter. Advantageously the dead volume of the airway adapter for neonates should be much less than 1 ml or even better than 0.5 ml, but preferably much less than 0.25 ml.

Table 2 shows calculated values how the mechanical dead volume of the airway adapter 132 and the branching unit 102 configuration of the embodiment increases proportional to the size of the subject. Notice that the total dead volume in table 2 is the same with the dead volume of airway adapter since the connection between the airway adapter and the branching unit can overlap completely.

TABLE 2

| Endotracheal tube ID [mm] | Dead Volume [ml] | | | |
|---|---|---|---|---|
| | Airway adapter | Branching unit | Total | |
| 2 | 0.39 | 0.05 | 0.39 | |
| 2.5 | 0.40 | 0.05 | 0.40 | |
| 3 | 0.42 | 0.05 | 0.42 | |
| 3.5 | 0.44 | 0.05 | 0.44 | Neonatal |
| 4 | 0.46 | 0.05 | 0.46 | |
| 4.5 | 0.49 | 0.05 | 0.49 | |
| 5 | 0.66 | 0.10 | 0.66 | |
| 5.5 | 0.72 | 0.10 | 0.72 | |
| 6 | 0.79 | 0.10 | 0.79 | Pediatric |
| 6.5 | 0.86 | 0.10 | 0.86 | |
| 7 | 0.93 | 0.10 | 0.93 | |

Since the end 111 of the endotracheal tube 101 outside the subject is cut off as close to the subject as possible it's dead volume can be excluded. Airway adapters 132 shown in the table 2 have been designed so that the airway adapters suitable for neonates fit into the branching unit 102 that is also designed for neonates. The inner diameter for the combination as parts are connected together is the maximum of 5 mm. Airway adapters 132 suitable for pediatrics that fit into the branching unit 102 designed for pediatrics has the maximum inner diameter of 7 mm for the combination as parts are connected together. This design ensures that the airway adapter 132 or the branching unit 102 has the minimum dead volume, but the maximum inner diameter to get minimum flow resistance in regard to the endotracheal tube 101, thus avoiding bottlenecks in the breathing gas flow path. This design also degreases the number of accessories to eleven different airway adapters 132 and two different branching units 102 for neonates and pediatrics. Thus the total dead volume for the airway adapter 132 used with the mainstream gas analysis in connection with the branching unit 102, according to the embodiment, which are also in connection through endotracheal tube with inner diameter of 2.5 mm to the patient that weights 2 kg is approximately 0.4 ml. This is approximately $\frac{1}{25}$ of the TV of 8-14 ml of the subject in the example. As a conclusion the subject is possibly more likely to get a better treatment as the airway adapter 132 of the embodiment is used. Due to the reduction of dead volume it is also possible to ventilate the subject at lower frequencies, less than 200 breaths/min, with conventional ventilators, which in turn ensures a good oxygenation of the subject, as it is possible to analyze the breathing gas in the airway adapter 132 in real time and then to control the ventilator 107 accurately in the control loop also in real time.

Very low mechanical dead volume airway adapter 132 for the gas analyzer 103 and the branching unit 102 configuration ensures that even the smallest subjects can be ventilated with conventional ventilators 107, that function at respiration rates less than 200 breaths/min, but also the gas monitored to ensure a proper gas exchange at the alveoli and improved controlling of ventilator 107, thus improving the treatment of the subject considerably.

The endotracheal tubes 101 may be integrated into the airway adapters 132 or branching units 102, but preferably they are separate parts, since as the patient is intubated the part of the endotracheal tube 101 sticking out from the oral or nasal cavity of the subject, in other words a mouth or a nose, may be cut shorter to minimize the mechanical dead volume of the endotracheal tube itself. After the endotracheal tube 101 is cut shorter the airway adapter 132 or the branching unit 102 can be connected to the endotracheal tube 101 by pushing it against the endotracheal tube 101 so that an end 111 of the endotracheal tube 101 slides and tightens on the connector 134 as shown in a schematic view in FIG. 6.

Similarly the airway adapter 132 may be integrated into the branching unit 102, in which case its common dead space might be lower than that they are separate, but preferably they are separate parts so that it may be possible to connect the endotracheal tube 101 straight into the third limb 121 of the branching unit 102 to minimize the mechanical dead volume in the case the gas analyzer 103 is not used.

Figure 6:
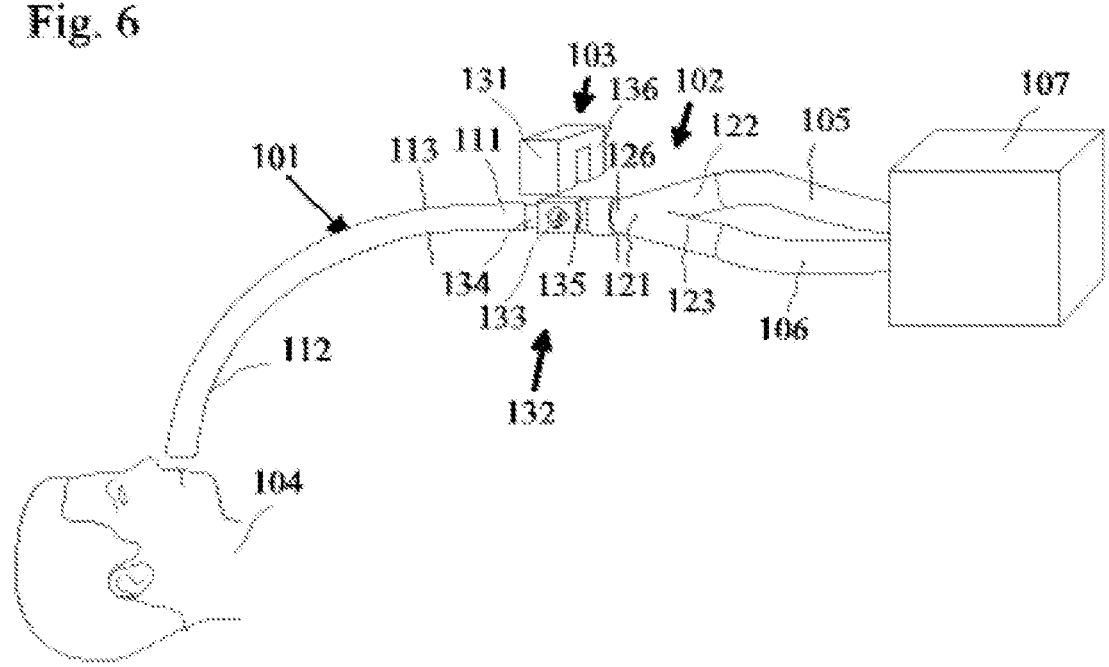
FIG. 6 shows a breathing circuit of FIG. 3 and its dead volume when separate parts are connected together.

When the gas analyzer 103 is used, the airway adapter 132 is connected to the third limb 121 of the branching unit 102 through the connector 135 by pushing the airway adapter 132 towards the third limb 121 when the male type conically shaped tubular connector 135 slides in and tightens to a female type conically shaped end of the third limb 121 of the branching unit 102, which is also shown in FIG. 6. The third limb 121 and the connector 135 overlap each other as much as possible to minimize the dead volume in the connection, but they also form a continuous smooth cavity with a minimal step like a change in an inner diameter along the breathing gas flow path between the cavity of the airway adapter 132 and the branching unit 102.

Table 3 shows the differences in the dead volumes between different combinations of connecting or integrating the pieces together.

TABLE 3

| Patient | tube ID | Branching unit with a connection to endotracheal tube [ml] | Separate branching unit and airway adapter [ml] |
|---|---|---|---|
| Neo (min) | 2 | 0.03 | 0.39 |
| Neo (max) | 4.5 | 0.14 | 0.49 |
| Pedi (min) | 5 | 0.18 | 0.66 |
| Pedi (max) | 7 | 0.35 | 0.93 |

To complete the patient side of the breathing circuit so that breathing gases can be analyzed, the airway adapter 132 is connected into a cavity 136 of analyzer body 131, so that breathing gases flowing trough the smooth and continuous sampling chamber 133 of the airway adapter 132 can be analyzed by an analyzing circuit (not shown in the Figures) inside the analyzer body 131.

The dead volume of the breathing circuit configuration shown in FIG. 6 is the volume between the place 113 at the endotracheal tube 101 shown with a dashed line and an area close to a a branching point 126 of the inspiratory limb 122 and the expiratory limb 123 also shown with a dashed line. The place 113 is near the beginning of the nasal or oral cavity (the mouth or nose) of the subject 104, where the endotracheal tube 101 was cut shorter, but also close to the connector 134 of the airway adapter 103. The total dead volume of the breathing circuit, consisting the airway adapter 132 and the branching unit 102 or its third limb 121, should be less than 5 ml, but preferably less than 3 ml for pediatrics and less than 1 ml or even better than 0.5 ml, but preferably less than 0.25 ml for neonates. The total volume of the endotracheal tube 101 depends on the inner diameter and the length of this endotracheal tube, which in turn depends on the size of the subject where it is connected.

The written description uses examples to disclose embodiments of the invention, including the best mode, and also to enable any person skilled in the art to make and use the invention. The patentable scope of the claimed invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A branching unit for delivering a respiratory gas of a subject, the branching unit comprising:
   a first limb configured to deliver an expiratory gas during an expiratory phase;
   a second limb configured to deliver an inspiratory gas during an inspiratory phase;
   a third limb configured to deliver both said expiratory gas and said inspiratory gas;
   a common branching point for said first limb, said second limb and said third limb; and
   an airway adapter defining a connector;
   wherein one limb of said first limb, second limb and third limb is connectable to the connector of the airway adapter to form a connection where the one limb and the connector overlap completely when connected to reduce dead volume in the connection, and
   wherein said first limb, said second limb and said third limb include a volume for said respiratory gas and which volume includes both an active volume with the gas exchanging between said inspiratory phase and said expiratory phase and a dead volume for the respiratory gas with insufficient gas exchange from said inspiratory phase to said expiratory phase and said dead volume being less than 1 ml.

2. The branching unit according to claim 1, wherein said dead volume is less than 0.5 ml for pediatric and less than 0.2 ml for neonate.

3. The branching unit according to claim 1, wherein said dead volume is located in said third limb.

4. The branching unit according to claim 1, wherein the one limb of said first limb, second limb and third limb and the airway adapter define a common dead volume of less than 5 ml when connected to each other.

5. The branching unit according to claim 1, wherein said third limb is connectable to an endotracheal tube.

6. The branching unit according to claim 4, wherein said airway adapter's dead volume is less than 3 ml.

7. The branching unit according to claim 4, wherein said airway adapter comprises a sampling chamber and an optical windows and is configured to receive a gas analyzer for measuring at least one gas component flowing through said sampling chamber.

8. The branching unit according to claim 1, wherein a mean inner cross-sectional area of said third limbs is between 80 mm$^2$ and 38 mm$^2$ for pediatrics, and between 44 mm$^2$ and 16 mm$^2$ for neonates.

9. The branching unit according to claim 4, wherein a mean inner cross-sectional area of said airway adapter is less than 44 mm$^2$ especially for pediatrics, and less than 20 mm$^2$ for neonates.

10. The branching unit according to claim 1, wherein a cross-sectional area of said third limb is designed with a size of a subject group, so that said cross sectional area is smaller for neonates, larger for pediatrics and largest for adults.

11. The branching unit according to claim 1, wherein said third limb defines different designs for different subject groups, so that said dead volume of said third limb is increasing when a size of the subject group is increasing.

12. An apparatus for delivering a respiratory gas of a subject, the apparatus comprising:
   a branching unit having a first limb configured to deliver an expiratory gas during an expiration phase, a second limb configured to deliver an inspiratory gas during an inspiratory phase, a third limb configured to deliver both said expiratory gas and said inspiratory gas and a common branching point for said first limb, said second limb and said third limb; and
   an airway adapter defining a connector, a sampling chamber and an optical window, said airway adapter configured to receive a gas analyzer for measuring at least one gas component of said respiratory gas and which said airway adapter is in flow communication with said branching unit,
   wherein one limb of the branching unit is connectable to the connector of the airway adapter to form a connection where the one limb and the connector overlap completely when connected to reduce dead volume in the connection, and
   wherein said branching unit and said airway adapter together include a volume for said respiratory gas and which volume includes both an active volume with the gas exchanging between said inspiratory phase and said expiratory phase and a dead volume for the respiratory gas with insufficient gas exchange from said inspiratory phase to said expiratory phase and said dead volume being less than 5 ml.

13. An apparatus according to claim 12, wherein said dead volume of said airway adapter and said branching unit together is less than 3 ml.

* * * * *